United States Patent
Zhang

(10) Patent No.: US 7,031,763 B1
(45) Date of Patent: Apr. 18, 2006

(54) MRI SHOULDER COIL

(75) Inventor: Vera Fengling Zhang, Streetsboro, OH (US)

(73) Assignee: General Electric Company, Schenectady, NY (US)

( * ) Notice: Subject to any disclaimer, the term of this patent is extended or adjusted under 35 U.S.C. 154(b) by 495 days.

(21) Appl. No.: 10/125,157

(22) Filed: Apr. 18, 2002

Related U.S. Application Data

(60) Provisional application No. 60/284,477, filed on Apr. 18, 2001.

(51) Int. Cl.
*A61B 5/055* (2006.01)

(52) U.S. Cl. ............................ 600/422; 324/318
(58) Field of Classification Search ............ 600/410, 600/422; 324/318, 322, 309
See application file for complete search history.

(56) References Cited

U.S. PATENT DOCUMENTS

| | | | |
|---|---|---|---|
| 5,136,244 A * | 8/1992 | Jones et al. | 324/318 |
| 5,143,068 A | 9/1992 | Muennemann et al. | |
| D350,825 S | 9/1994 | Lee | |
| 5,343,862 A | 9/1994 | Jones | |
| 5,351,688 A | 10/1994 | Jones | |
| 5,575,287 A * | 11/1996 | Eydelman | 600/422 |

* cited by examiner

*Primary Examiner*—Ruth S. Smith
(74) *Attorney, Agent, or Firm*—Carl B. Horton, Esq.; Armstrong Teasdale LLP

(57) ABSTRACT

A MRI quadrature coil for imaging a human shoulder has a first coil shaped to conform to the top of the shoulder and a second coil adapted to encircle the shoulder. The second coil has a magnetic axis generally orthogonal to that of the first coil.

20 Claims, 4 Drawing Sheets

MRI SHOULDER COIL

CROSS-REFERENCE TO RELATED APPLICATION

This application claims the benefit of U.S. provisional patent application Ser. No. 60/284,477 filed Apr. 18, 2001.

BACKGROUND OF THE INVENTION

The present invention relates to magnetic resonance imaging (MRI) radio frequency (RF) coils and, in particular, to a coil for imaging a human shoulder.

MRI utilizes hydrogen nuclear spins of the water molecules in the human body, which are polarized by a strong, uniform, static magnetic field of the main magnet (named $B_0$—the main magnetic field in MRI physics). The magnetically polarized nuclear spins generate magnetic moments in the human body. The magnetic moments point in the direction of the main magnetic field in a steady state, and produce no useful information if they are not disturbed by any excitation.

The generation of a nuclear magnetic resonance (NMR) signal for MRI data acquisition is accomplished by exciting the magnetic moments with a uniform RF magnetic field (called the $B_1$ field or the excitation field). The $B_1$ field is produced in the imaging region of interest by an RF transmit coil which is driven by a computer-controlled RF transmitter with a power amplifier. $B_0$ and $B_1$ refer to the magnetic axes of the fields. During excitation, the nuclear spin system absorbs magnetic energy, and it's magnetic moments process around the direction of the main magnetic field. After excitation, the processing magnetic moments will go through a process of free induction decay (FID), releasing their absorbed energy and returning to the steady state. During FID, NMR signals are detected by the use of a receive RF coil, which is placed in the vicinity of the excited volume of the human body. The NMR signal is the secondary electrical voltage (or current) in the receive RF coil that has been induced by the precessing magnetic moments of the human tissue. The receive RF coil can be either the transmit coil itself, or an independent receive-only RF coil. The NMR signal is used for producing magnetic resonance images by using additional pulsed magnetic gradient fields, which are generated by gradient coils integrated inside the main magnet system. The gradient fields are used to spatially encode the signals and selectively excite a specific volume of the human body. There are usually three sets of gradient coils in a standard MRI system, which generate magnetic fields in the same direction as the main magnetic field, varying linearly in the imaging volume.

In MRI, it is desirable for the excitation and reception to be spatially uniform in the imaging volume for better image uniformity. In a standard MRI system, the best excitation field homogeneity is usually obtained by using a whole-body volume RF coil for transmission. The whole-body transmit coil is the largest RF coil in the system. A large coil, however, produces a lower signal-to-noise ratio (SNR) if it is also used for reception, mainly because of its greater distance from the signal-generating tissues being imaged. Since a high signal-to-noise ratio is the most desirable in MRI, special-purpose coils are used for reception to enhance the SNR ratio from the volume of interest.

In practice, a well-designed specialty RF coil should have the following functional properties: high SNR, good uniformity, sufficient coverage and penetration, a high unloaded quality factor (Q) of the resonance circuit, and a high ratio of the unloaded to loaded Q factors. In addition, the coil device should be mechanically designed to facilitate patient handling and comfort, and to provide a protective barrier between the patient and the RF electronics. Another way to increase the SNR is by quadrature phased array reception. In this method, NMR signals are detected in two orthogonal directions, which are in the transverse plane or perpendicular to the main magnetic field. The two signals are detected by two independent individual coils that cover the same volume of interest. With quadrature reception, the SNR can be increased by up to a factor of the square root of two over that of individual linear coils.

Imaging a human shoulder should include imaging and visualization of the shoulder girdle including glenoid fossa, labrum, humeral head, neck and body, supraspinatus, infraspinatus and teres minor insertion (rotator cuff) and surrounding soft tissues. Shoulder imaging comprises approximately 20% of all MRI done. Most of these examinations are done for the following reasons:

a). R/O rotator cuff tear (new or current)
b). R/O labral tear or deterioration
c). R/O impingement syndrome The radiographical applications associated with the evaluation of shoulder anatomy are conventional X-ray and X-ray anthrography, sometimes enhanced with contrast agents. MRI shoulder imaging has been used in place of X-ray anthrograms and combined X-ray and enhanced CT scans. The main reasons for MRI as a preferred modality is reduction of patient exposure to ionizing radiation and iodinated contrast agents. Therefore, MRI examinations of the shoulder are better for a patient in terms of morbidity and is more cost effective for the health provider.

Several problems exist in existing MRI shoulder coils. In a horizontal bore MRI scanners, the quadrature coils of U.S. Pat. Nos. 5,343,862 and 5,351,688) do not provide optimized SNR due to the required separation of the anterior and posterior elements. The separation between the anterior and posterior elements needs to be sufficient in order to avoid strong coupling to each other. Strong coupling to each other will result in poor isolation and therefore poor combined image quality. Keeping the two elements far enough apart so that the sensitivity at the middle region becomes weak enough to maintain acceptable isolation will lead to poor penetration in combined image.

Open MRI scanners where the $B_0$ direction is vertical are especially good for shoulder imaging due to the following reasons:

(1) Large size patients who cannot fit into the small-bore horizontal scanners are more easily accommodated in vertical open MRI scanners.
(2) People who suffer from claustrophobia find more comfort in open MRI scanners.
(3) Open MRI scanners have an advantage in scanning large athletic males, typically evaluated for sports related injury. The shoulder under study can be positioned at iso-center of the scanner where the images have the best quality. Unfortunately, the shoulder coils described in U.S. Pat. Nos. 5,343,862 and 5,351,688 will not function in open MRI scanners because of the direction of the magnetic axes of the disclosed coils.

U.S. Patent No. Des. 350,825 and U.S. Pat. No. 5,143,068 use linear loop coils. The linear coil can have good signal at center of the loop, but the coverage, uniformity and penetration are too poor for adequate clinical application, even at the humeral head, the center of region of interest for shoulder imaging.

SUMMARY OF THE INVENTION

A MRI quadrature coil for imaging a human shoulder has a first coil shaped to conform to the top of the shoulder and a second coil adapted to encircle the shoulder. The second coil has a magnetic axis generally orthogonal to that of the first coil.

DESCRIPTION OF THE PREFERRED EMBODIMENTS

Figure 1:
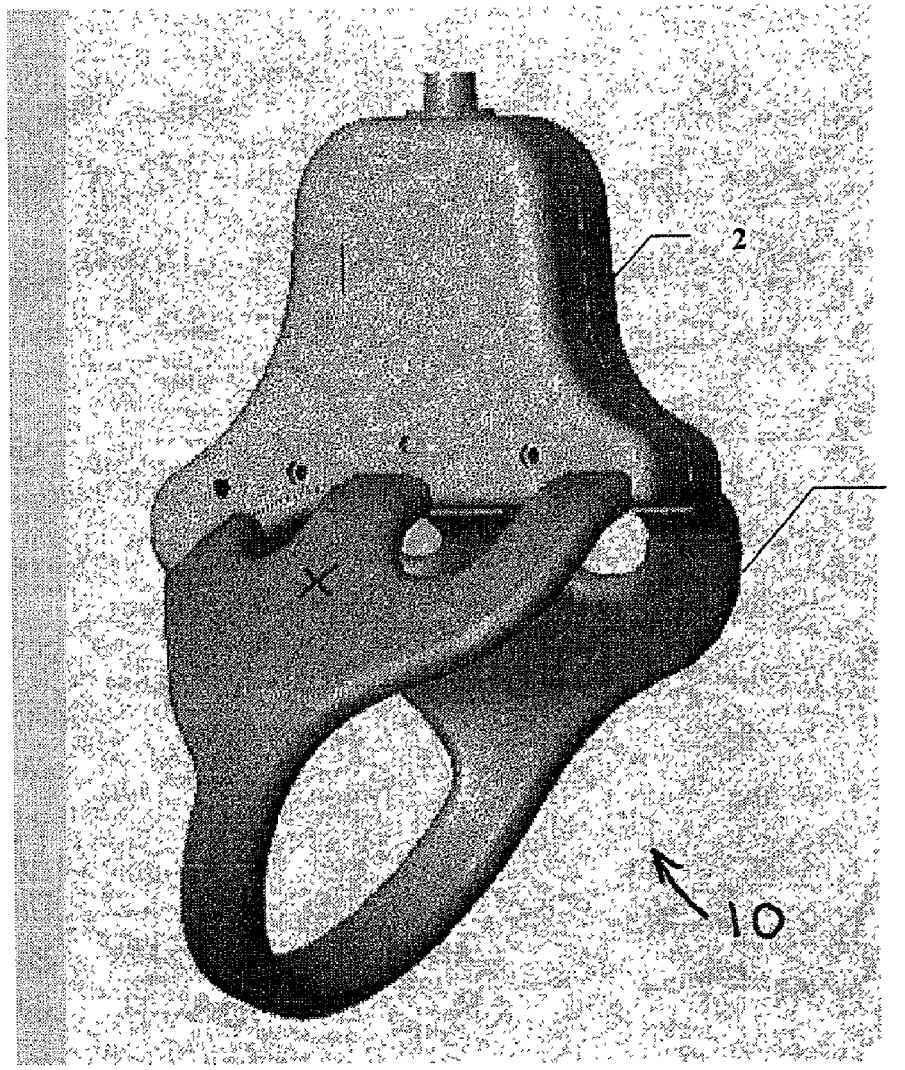
FIG. 1 is a perspective view of a coil according to the invention

Referring to FIG. 1, a quadrature coil 10 for a human shoulder includes a frame 1 and a housing 2. The frame 1 may be, for example, formed of flexible plastic, covered with soft foam and coated with a smooth vinyl. The frame 1 is optimized for conforming to the top of a human shoulder. It may be produced, for example, in three sizes (e.g., small, medium, large) to a enable imaging of 100 percent of the patient population. The housing 2 may be, for example, formed of a rigid plastic. As more fully described below, the electrical components of the coil may be located within the frame 1 and housing 2.

Figure 2:
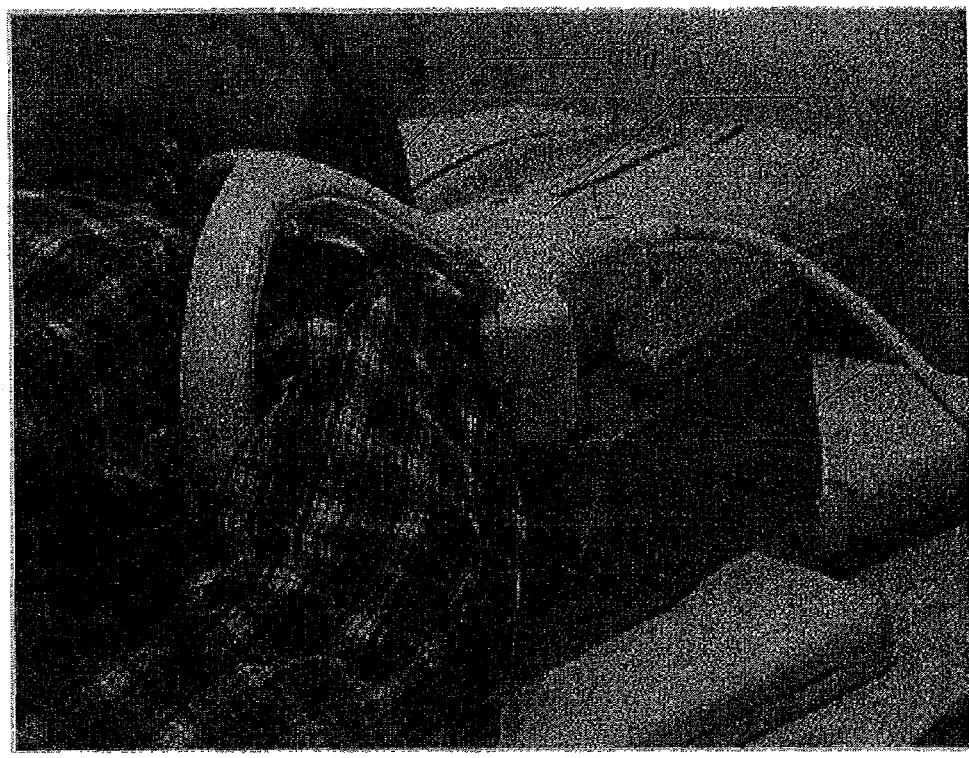
FIG. 2 is a perspective view of a coil according to the invention positioned on a patient.

Referring to FIG. 2, the coil 10 is shown positioned on a human shoulder for imaging. A foam pad 3, for example, may be used on the left side of the patient to help position the coil 10 on the patient. To image the other shoulder of the patient, the coil 10 may be inverted and a similar foam pad but with a reversed left-right symmetry used.

Figure 3:
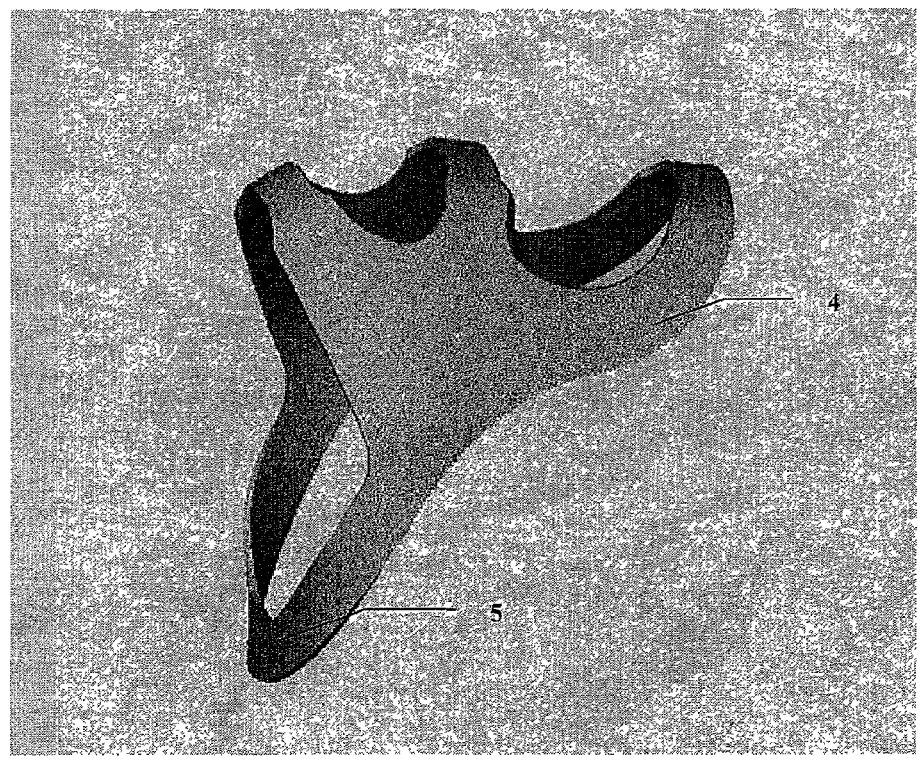
FIG. 3 is a perspective view of a flexible support frame for a coil according to the invention.

Referring to FIG. 3, a possible mechanical structure 4 within the frame 1 is shown. The underarm portion 5 of the structure 4 may be twisted 90 degrees for patient comfort.

Figure 4:
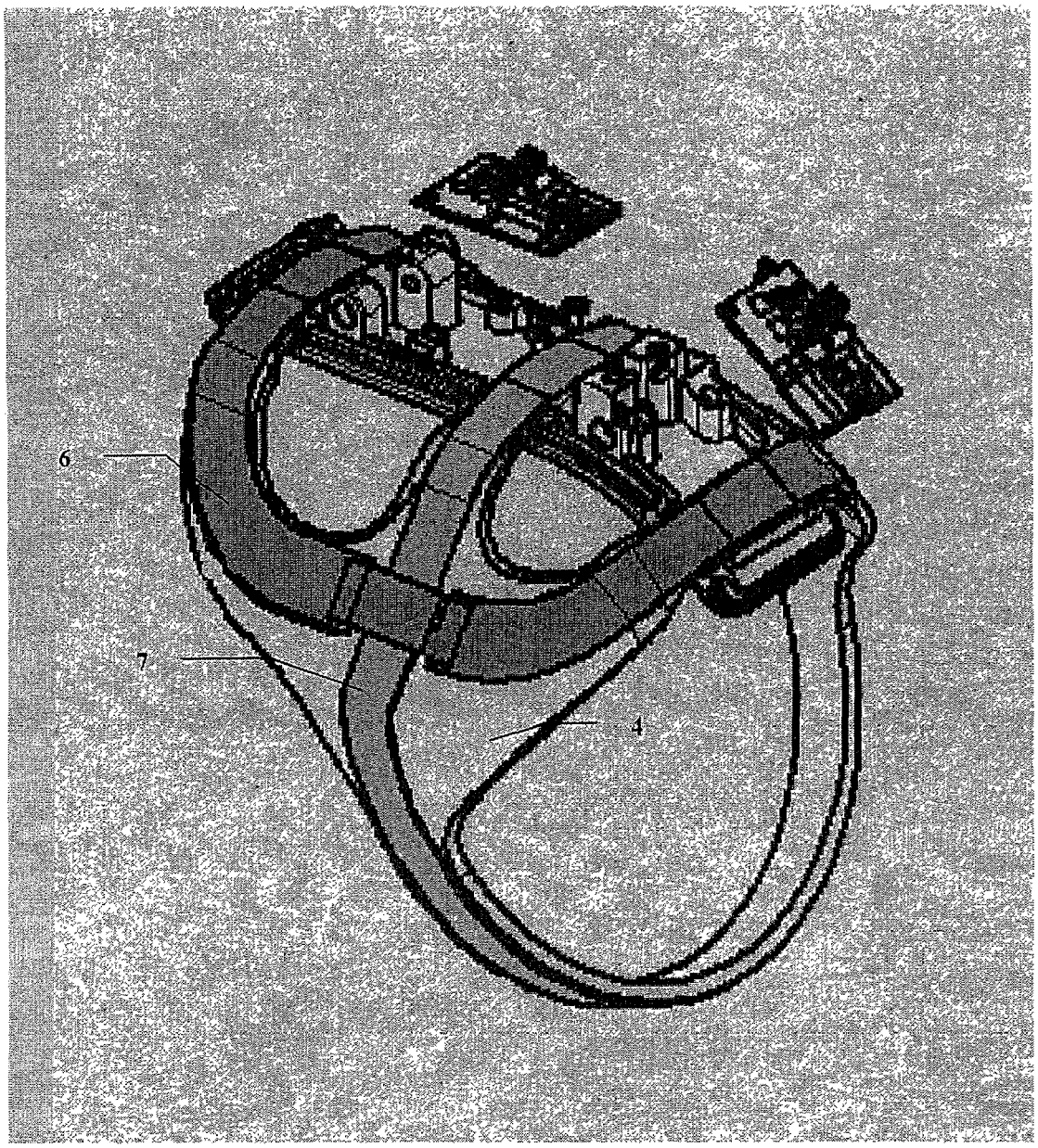
FIG. 4 is a perspective view of a possible electrical configuration of a coil according to the invention.

Referring to FIG. 4, a possible electrical configuration of the coil 10 is shown. This configuration is useful in an open MRI system. The uniform, static magnetic field of the magnet $B_0$ direction for an open MRI system is vertical (e.g, chest to back). The coil 10 may be a receive only coil.

The coil 10 has two coils, a halo or loop coil 6 and an underarm loop coil 7. The coil 6 conforms to the shape of the top of the shoulder, extending partially down the front and back of the shoulder. The coil 7 allows the patient's arm to be inserted through the coil 10, encircling the shoulder when moved to the patient's armpit. The coil 7 may be, for example, tangent to and bisecting the coil 6.

The angle between the upper region of the underarm channel and the lower region may be, for example, about 152 degrees. The angle between the coil 6 and the coil 7 may be, for example, about 100 degrees. The two coils 6, 7 are not orthogonal to each other geometrically, however the surfaces are curved in such a way that the B flux from the two channels is orthogonal in the 3-D volume. This orthogonality permits the coil 10 to operate as a quadrature coil.

The coils 6, 7 may be, for example formed from copper tape, the width, thickness and number of turns being chosen for optimized sensitivity.

The housing 1 may be used to cover, enclose and support electronic components which are electrically connected to the coils 6, 7 and provide a means of tuning the coils.

The coil 6 ucovers from left to right, from the neck end of the clavicle bone to the head of the humerus, providing signal from the clavicle bone, the acromion bone, the coranoid process and the glenoid cavity. The coil 7 from superior to inferior adds in significant signal from the humeral head and neck, the cromion bone, the coranoid process, the glenoid cavity, the supraspinatus, the infraspinatus, the rotator cuff and surrounding soft tissues. The two coils together produce images with clear definition of the shoulder joint, large coverage, sufficient penetration, and good uniformity.

Figure 5:
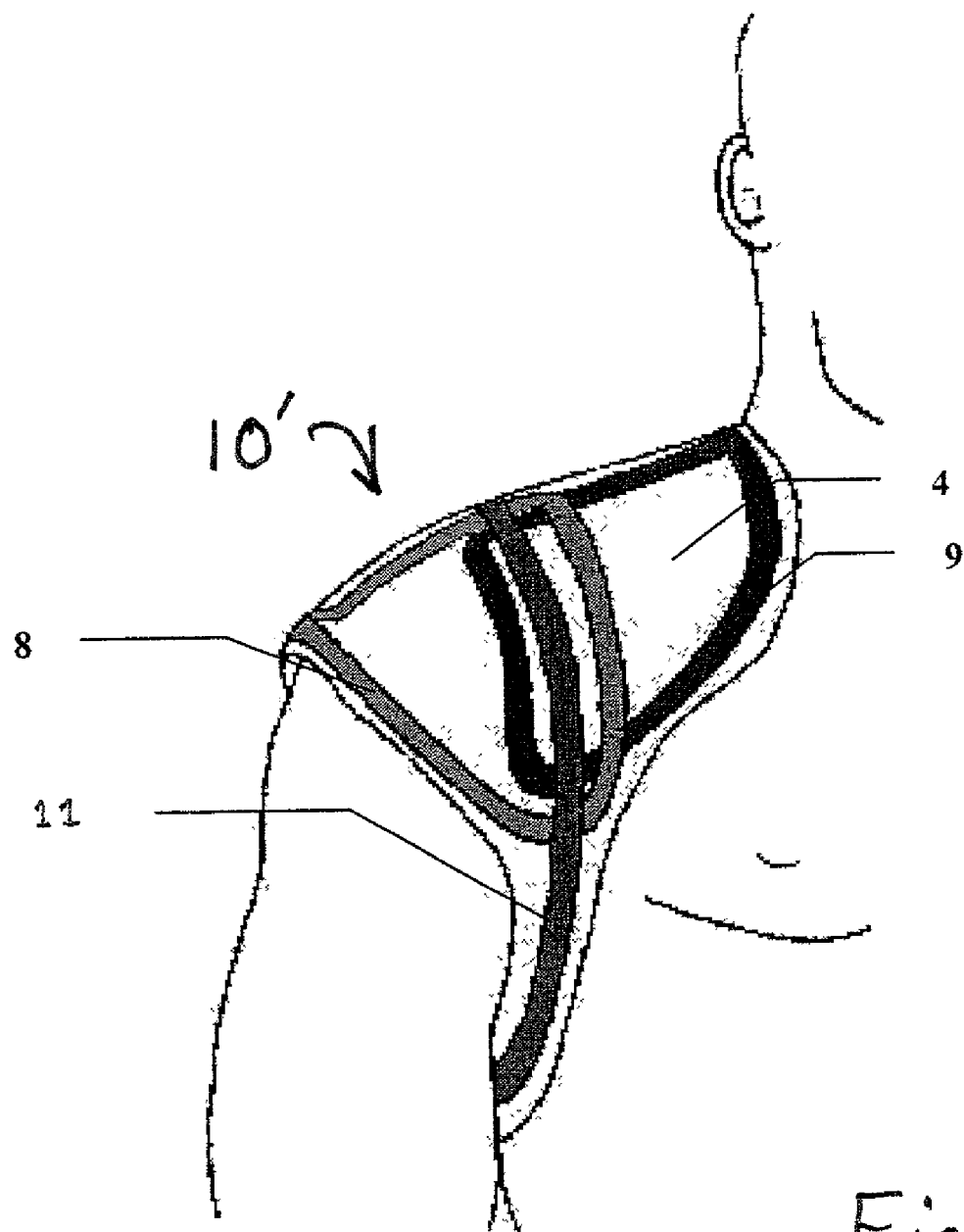
FIG. 5 is a perspective view of another possible electrical configuration of a coil according to the invention.

Referring to FIG. 5, the coil 10' is suitable for a horizontal bore MRI system, such as a superconductor MRI system. The direction of the uniform static magnetic field ($B_0$) for a superconductor MRI is horizontal (in the superior-inferior direction of the patient). The coil 10, may be, for example, a receive only coil. Similar to the coil 10, the coil 10' may include a soft foamed and vinyl coated frame and a rigid housing, and may be electrically constructed of copper tape.

The coil 10' may be implemented with two Helmholtz coil elements 8, 9 and one underarm loop coil 11. The coil elements 8, 9 conform to the shape of the top of the shoulder, extending partially down the front and back of the shoulder. The coil 11 allows the patient's arm to be inserted through the coil 10', encircling the shoulder when moved to the patient's armpit.

The coil 11 may be, for example, positioned between the coil elements 8, 9 in the left to right direction and extends at an angle of 100 degrees from the coil elements 8, 9 in the inferior direction. The angle between the upper region of the coil 11 and the lower region may be, for example, about 152 degrees. The coil 10' may provide the same coverage of anatomy as the coil 10. However, the coil 6 has been replaced with two Helmholtz coils 8, 9.

The coils 8, 9 provide $B_1$ sensitivity in the vertical direction (anterior-posterior). Isolation between the two Helmholtz coils is provided by critical coupling, i.e. the overlap of the two elements is optimized to minimize coupling between the two channels. This allows the two Helmholtz coil elements to operate as an array coil. The coil 10 provides $B_1$ sensitivity in the left-right horizontal direction. Isolation between the Helmholtz coils and the underarm loop coil is achieved by the orthogonal relationship of the coil 11 to the coils 8, 9. This orthogonality permits the coil 10' to operate as a quadrature coil.

Similar to the coil 10, a housing may be used to cover, enclose and support electronic components which are electrically connected to the coils 8, 9, 11 and provide a means of tuning the coils.

It should be evident that this disclosure is by way of example and that various changes may be made by adding, modifying or eliminating details without departing from the fair scope of the teaching contained in this disclosure. The invention is therefore not limited to particular details of this disclosure except to the extent that the following claims are necessarily so limited.

What is claimed:

1. A MRI quadrature coil for imaging a human shoulder, said shoulder having a superior portion, said quadrature coil comprising:

a first coil arcuately shaped to conform to and extend over said superior portion of said shoulder from a chest portion to a shoulder blade portion, said first coil having a magnetic axis; and a second coil adapted to encircle said shoulder, said second coil having a magnetic axis generally orthogonal to said first coil magnetic axis.

2. A MRI quadrature coil according to claim 1, wherein said first coil includes a loop coil element and said second coil includes a loop coil element.

3. A MRI quadrature coil according to claim 1, wherein said first coil includes a Helmholtz coil element and said second coil includes a loop coil element.

4. A MRI quadrature coil according to claim 3, wherein said first coil further includes another Helmholtz coil element, said first coil being an array coil.

5. A MRI quadrature coil according to claim 1, wherein said coils are flexible.

6. A MRI quadrature coil according to claim 1, further comprising a rigid housing, said first and second coils extending therefrom.

7. A MRI quadrature coil according to claim 1, wherein said first and second coils are mounted on a common flexible frame.

8. An imaging system for imaging a shoulder of a body, said imaging system comprising:
   a first coil configured to conform to and extend over a superior portion of the shoulder from a chest portion to a shoulder blade portion; and
   a second coil separate from the first coil and configured to encircle the shoulder.

9. An imaging system according to claim 8, wherein said first coil has a magnetic axis orthogonal to a magnetic axis of said second coil.

10. An imaging system according to claim 8, wherein said imaging system comprises a magnetic resonance imaging system.

11. An imaging system according to claim 8, wherein said first coil comprises Helmholtz coil elements.

12. An imaging system according to claim 8, wherein said second coil encircles the shoulder when an arm of the body is inserted through the second coil.

13. An imaging system according to claim 8, wherein said first coil extends from an end of a clavicle bone of the body to an end of a humerus bone of the body.

14. An imaging system according to claim 8, wherein said first coil comprises Helmholtz coil elements, and the second coil is located between a portion of a first of the Helmholtz coil elements and a portion of a second of the Helmholtz coil elements.

15. A method for imaging, said method comprising:
   providing a first coil;
   providing a second coil separate from the first coil;
   conforming the first coil to extend over a superior portion of a shoulder of a body and partially down a front and a back of the shoulder across an axis from a neck end of a clavicle bone to a head of a humerus bone; and
   configuring the second coil to encircle the shoulder.

16. A method according to claim 15, further comprising configuring the first coil to have a magnetic axis orthogonal to a magnetic axis of the second coil.

17. A method according to claim 15, wherein said providing the first coil comprises providing a pair of Helmholtz loop elements.

18. A method according to claim 15, wherein said configuring the second coil comprises configuring the second coil to encircle the shoulder when an arm of the body is inserted through the second coil.

19. A method according to claim 15, wherein said providing the first coil comprises providing a pair of Helmholtz loop elements, and further comprising positioning the second coil between a portion of a first of the Helmholtz loop elements and a portion of a second of the Helmholtz loop elements.

20. A method according to claim 15 further comprising configuring the first coil to extend from an end of a clavicle bone of the body to an end of a humerus bone of the body.

* * * * *